(12) United States Patent
Okada (10) Patent No.: US 9,307,964 B2
(45) Date of Patent: Apr. 12, 2016

(54) INTRA-BODY-CAVITY INSERTION INSTRUMENT FASTENER

(75) Inventor: Yuta Okada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 874 days.

(21) Appl. No.: 12/606,471

(22) Filed: Oct. 27, 2009

(65) Prior Publication Data

US 2010/0048997 A1    Feb. 25, 2010

Related U.S. Application Data

(63) Continuation of application No. PCT/JP2008/058947, filed on May 15, 2008.

(30) Foreign Application Priority Data

May 18, 2007 (JP) ................................. 2007-133007

(51) Int. Cl.
| | |
|---|---|
| *A61B 17/00* | (2006.01) |
| *A61B 19/00* | (2006.01) |
| *A61B 17/29* | (2006.01) |
| *A61B 17/34* | (2006.01) |
| *A61B 17/28* | (2006.01) |

(52) U.S. Cl.
CPC ............ *A61B 17/00234* (2013.01); *A61B 19/26* (2013.01); *A61B 17/29* (2013.01); *A61B 17/34* (2013.01); *A61B 2017/003* (2013.01); *A61B 2017/2808* (2013.01)

(58) Field of Classification Search
CPC ........................... A61B 17/00; A61B 17/32056
See application file for complete search history.

(56) References Cited

U.S. PATENT DOCUMENTS

| | | | | |
|---|---|---|---|---|
| 4,598,699 A | * | 7/1986 | Garren et al. .................. | 606/185 |
| 5,224,680 A | * | 7/1993 | Greenstein et al. ......... | 248/316.4 |
| 5,300,082 A | * | 4/1994 | Sharpe et al. .................. | 606/147 |
| 5,318,564 A | * | 6/1994 | Eggers ............................ | 606/47 |
| 5,624,381 A | * | 4/1997 | Kieturakis .................... | 600/206 |
| 5,688,276 A | * | 11/1997 | Shaffer ......................... | 606/916 |
| 5,810,845 A | * | 9/1998 | Yoon ............................ | 606/139 |

(Continued)

FOREIGN PATENT DOCUMENTS

| | | |
|---|---|---|
| JP | 5-15914 | 3/1993 |
| JP | 6-63061 | 3/1994 |

(Continued)

OTHER PUBLICATIONS

Japanese Office Action dated Jun. 26, 2012 issued in counterpart Japanese Patent Application No. 2007-133007.

(Continued)

*Primary Examiner* — Lynsey Crandall
(74) *Attorney, Agent, or Firm* — Scully, Scott, Murphy & Presser, P.C.

(57) ABSTRACT

An intra-body-cavity insertion instrument fastener includes an insertion section that is inserted into a body cavity and is held, partially exposed to outside of a human body, and a fastening section that fixes, to a predetermined position, a position of a predetermined point of an intra-body-cavity insertion instrument inserted into the body cavity from an insertion hole different from an insertion hole from which the insertion section is inserted into the body cavity. The fastening section is formed at a top end of the insertion section.

3 Claims, 7 Drawing Sheets

(56) References Cited

U.S. PATENT DOCUMENTS

| | | | |
|---|---|---|---|
| 5,813,976 A | | 9/1998 | Filipi et al. |
| 5,836,869 A | * | 11/1998 | Kudo et al. ............... 600/173 |
| 5,860,987 A | * | 1/1999 | Ratcliff et al. ............. 606/113 |
| 5,876,325 A | * | 3/1999 | Mizuno et al. ............. 600/102 |
| 5,984,939 A | * | 11/1999 | Yoon ........................... 606/170 |
| 6,149,642 A | * | 11/2000 | Gerhart et al. ................ 606/1 |
| 6,193,672 B1 | * | 2/2001 | Clement ..................... 600/565 |
| 6,346,106 B1 | * | 2/2002 | Jako ............................. 606/47 |
| 6,419,688 B1 | * | 7/2002 | Bacher et al. ............... 606/205 |
| 6,500,170 B2 | * | 12/2002 | Palmer et al. ................... 606/1 |
| 2006/0235426 A1 | * | 10/2006 | Lim et al. ....................... 606/99 |
| 2006/0253109 A1 | * | 11/2006 | Chu ................................. 606/1 |
| 2006/0259018 A1 | * | 11/2006 | Shilkrut ........................... 606/1 |

FOREIGN PATENT DOCUMENTS

| | | |
|---|---|---|
| JP | 8-38494 | 2/1996 |
| JP | 8-89504 | 4/1996 |
| JP | 8-275958 | 10/1996 |
| JP | 2002-017752 A | 1/2002 |
| JP | 2006-061272 A | 3/2006 |

OTHER PUBLICATIONS

Japanese Office Action dated Feb. 28, 2012 issued in counterpart Japanese Patent Application No. 2007-133007.

\* cited by examiner

INTRA-BODY-CAVITY INSERTION INSTRUMENT FASTENER

CROSS-REFERENCE TO RELATED APPLICATIONS

This is a Continuation Application of PCT Application No. PCT/JP2008/058947, filed May 15, 2008, which was published under PCT Article 21(2) in Japanese.

This application is based upon and claims the benefit of priority from prior Japanese Patent Application No. 2007-133007, filed May 18, 2007, the entire contents of which are incorporated herein by reference.

BACKGROUND OF THE INVENTION

1. Field of the Invention

The present invention relates to an intra-body-cavity insertion instrument fastener that fixes an intra-body-cavity insertion instrument inserted in an organism when performing a surgical operation.

2. Description of the Related Art

Recently, as minimally-invasive procedures which do not require a large incision, endoscopic surgical operations have been carried out in a manner that various procedures are performed in a body cavity by incising an opening in a wall of a human body such as an abdominal wall and by further inserting an endoscope or a surgical instrument into the body cavity through the opening.

As surgical instruments used for such endoscopic surgical operations, there are rigid surgical instruments in which an insertion section to be inserted into a body cavity is formed of a rigid tube, as well as pliable surgical instruments in which the insertion section is formed of a pliable tube, for example, as disclosed in Patent Document 1. When performing a procedure at a deep part (such as a back side of an organ) in a body cavity, pliable surgical instruments are used in general because the posture of the insertion section can be adjusted vertically in accordance with that the insertion section moved along the organ in the body cavity or the surgeon's manipulation and the insertion section can therefore be inserted into the body cavity while changing bending of the insertion section.

Patent Document 1: Jpn. UM Appln. KOKOKU Publication No. 5-15914

BRIEF SUMMARY OF THE INVENTION

Accordingly, the present invention provides an intra-body-cavity insertion instrument fastener by which an intra-body-cavity insertion instrument, which is deformed flexibly and easily inserted into a body cavity, is fixed when the intra-body-cavity insertion instrument is used.

According to one aspect of the invention, there is provided an intra-body-cavity insertion instrument fastener comprising: an insertion section that is inserted into a body cavity and is held, partially exposed to outside of a human body; and a fastening section that fixes, to a predetermined position, a position of a predetermined point of an intra-body-cavity insertion instrument inserted into the body cavity from an insertion hole different from an insertion hole from which the insertion section is inserted into the body cavity, that the fastening section is formed at a top end of the insertion section.

DETAILED DESCRIPTION OF THE INVENTION

Hereinafter, best mode for carrying out the present invention will be described with reference to the drawings.

First Embodiment

Figure 1A:
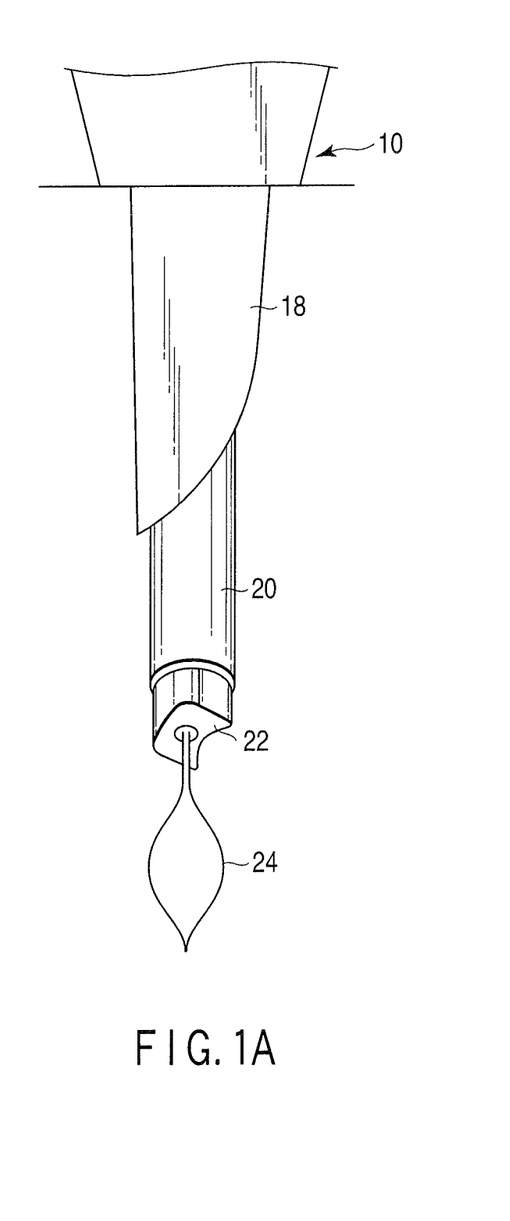
FIG. 1A is a perspective view illustrating a structure of an intra-body-cavity insertion instrument fastener according to the first embodiment of the present invention.
Figure 1B:
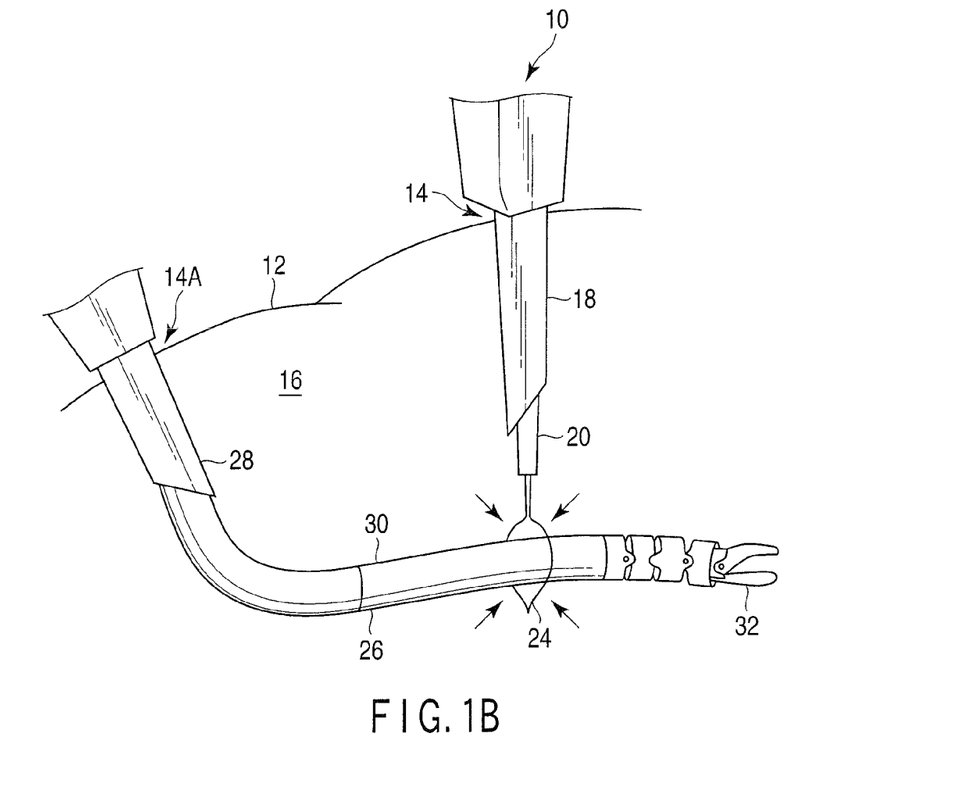
FIG. 1B is a view illustrating a state of use of the intra-body-cavity insertion instrument fastener.

FIG. 1A is a perspective view illustrating a structure of an intra-body-cavity insertion instrument fastener 10 according to the first embodiment of the invention. FIG. 1B illustrates a use state of the intra-body-cavity insertion instrument fastener 10.

The intra-body-cavity insertion instrument fastener 10 includes an insertion section 18 which is inserted into a body cavity 16 from an insertion hole 14 formed in a body wall 12 and is held in the body wall 12, partially exposed to outside of a human body. A sheath 20 is further protruded from a top end of the insertion section 18, and an arcuate groove section 22 is formed at the top end of the sheath 20. A snare loop 24 protrudes from the center of the groove section 22. The snare loop 24 is connected through the sheath 20 to a slider (not illustrated) provided on the insertion section 18, and is configured so as to tighten as the slider is pulled.

A pliable intra-body-cavity insertion instrument, e.g., a pair of pliable forceps 26 includes a pliable insertion section 30 and a forceps section 32 provided at a top end of the pliable insertion section 30. When used, the pair of pliable forceps 26 is inserted into a body cavity 16 from an insertion hole 14A formed in the body wall 12, and is further inserted into a target portion in the body cavity 16 through a trocar 28 fixed to the body wall 12. When the forceps section 32 reaches the target portion, operation of inserting the pair of pliable forceps 26 is then terminated, and a procedure is performed by the forceps section 32. In case of such pliable forceps 26, the pliable insertion section 30 is pliable and therefore allows access to a target portion such as a back side of an organ which cannot directly be accessed by rigid forceps. The pair of pliable forceps 26 also has an advantage that a procedure is easy even at other portions than a target portion very close to the insertion hole 14A toward the body cavity 16. However, when performing a procedure, a desired procedure cannot be performed or a target organ or any other organ in the periphery may be damaged by the forceps section 32 if the pliable insertion section 30 which supports the forceps section 32 moves.

Figure 1C:
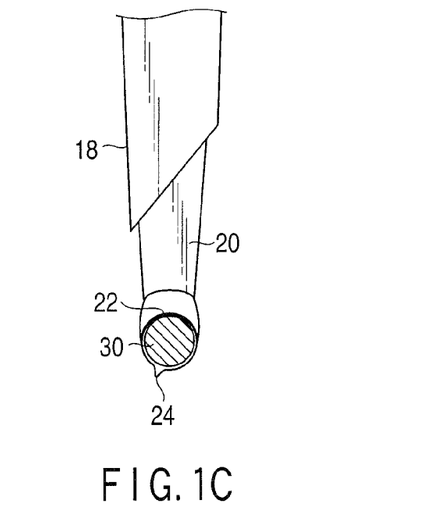
FIG. 1C is a view illustrating a state in which an intra-body-cavity insertion instrument is fixed.
Figure 2:
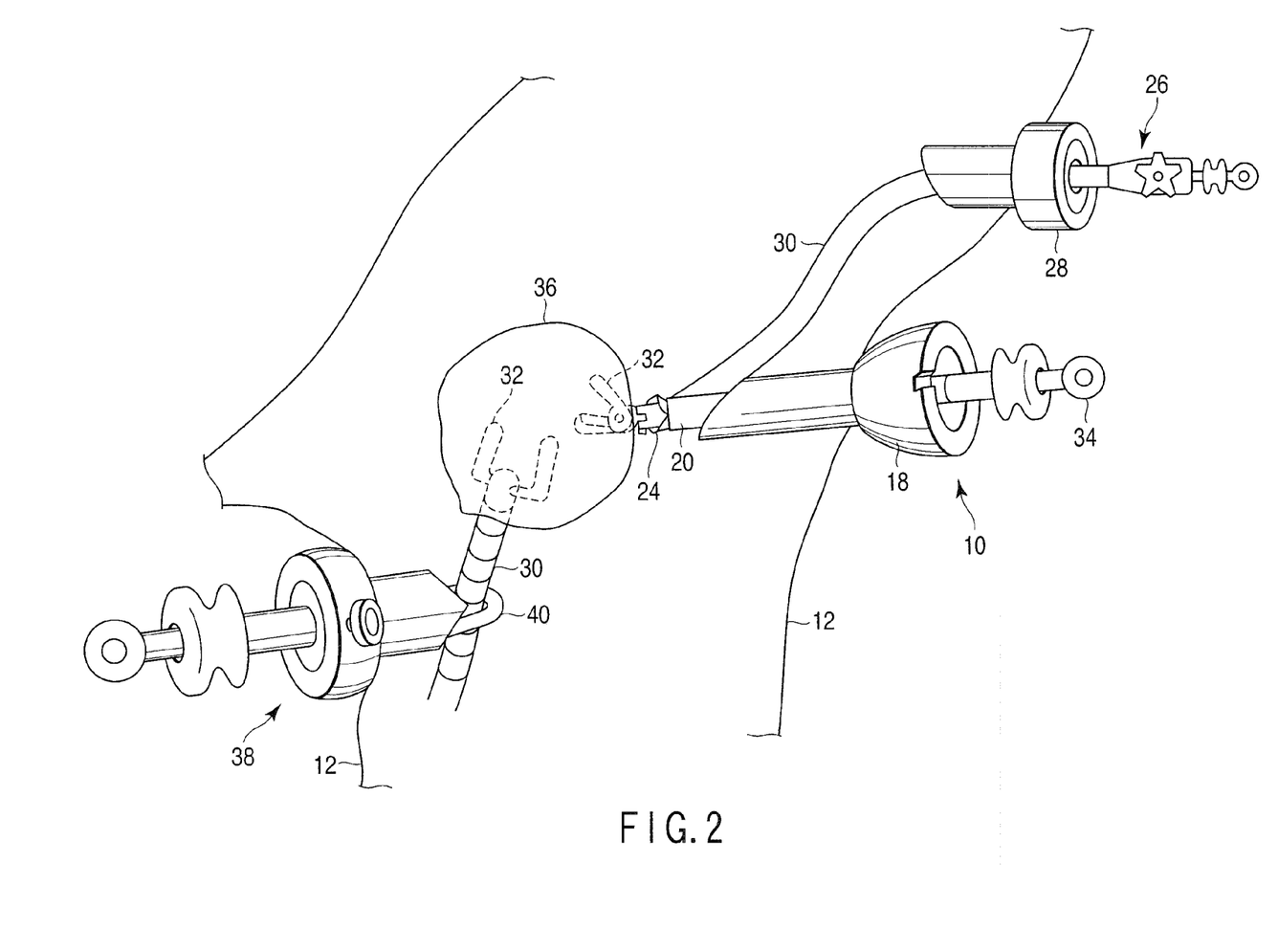
FIG. 2 is a view illustrating a state in which an intra-body-cavity insertion instrument is fixed by an intra-body-cavity insertion instrument fastener according to the first and second embodiments.

Hence, when inserting the pliable forceps 26, the intra-body-cavity insertion instrument fastener 10 according to the first embodiment is used, to insert the pliable insertion section 30 of the pair of pliable forceps 26 so as to extend through inside the snare loop 24, as illustrated in FIG. 1B. Further, when performing a procedure by the forceps section 32, a slider 34 of the intra-body-cavity insertion instrument fastener 10 as illustrated in FIG. 2 is pulled to tighten the loop of the snare loop 24, as denoted by arrows in FIG. 1B. As illustrated in FIG. 1C, a predetermined point of the pliable insertion section 30 of the pair of pliable forceps 26 is fixed to the groove section 22 formed at the top end of the sheath 20 of the intra-body-cavity insertion instrument fastener 10.

In this manner, the insertion section 18 of the intra-body-cavity insertion instrument fastener 10 is fixed to the body wall 12, and therefore, coordinates of the predetermined point of the pliable insertion section 30 of the pair of pliable forceps 26 is fixed, in the body cavity. Accordingly, a part defined between the body wall 12 and the predetermined point does not move when performing a procedure on a target portion of a target organ 36. Further, since a part from the predetermined point of the pliable insertion section 30 to the forceps section 32 can freely move, a procedure can be easily performed on the target portion. In this case, the predetermined point of the pliable insertion section 30 is grasped by the snare loop 24 of the intra-body-cavity insertion instrument fastener 10 to thereby engage the predetermined point of the pliable insertion section 30 in the groove section 22 of the sheath 20. Therefore, direction of the pliable insertion section 30 is constant relative to the sheath 20, and fixing force thereof is large.

Needless to say, a position at which the intra-body-cavity insertion instrument fastener 10 is inserted in the body wall 12 is determined in accordance with a position to which the predetermined point of the pliable insertion section 30 is to be fixed. In other words, the position of the predetermined point where the pliable insertion section 30 is fixed can be set arbitrarily. Accordingly, the fixing position attained by the intra-body-cavity insertion instrument fastener 10 can be arranged at an arbitrary position even if there is no adequate organ to which the pair of pliable forceps 26 in the body cavity is to be fixed. A procedure therefore can be performed stably.

As has been described above, the intra-body-cavity insertion instrument fastener 10 according to the first embodiment is fixed to the body wall 12. Therefore, if a pliable intra-body-cavity insertion instrument, e.g., the pair of pliable forceps 26 is inserted into a human body to perform a procedure, the pair of pliable forceps 26 can be prevented from moving during the procedure, by fixing the pliable forceps 26 to the intra-body-cavity insertion instrument fastener 10.

Second Embodiment

Figure 3A:
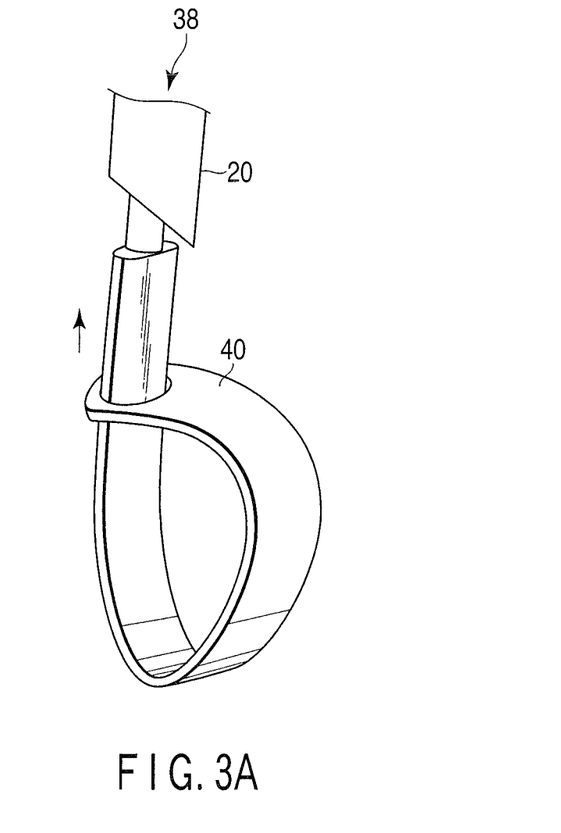
FIG. 3A is a perspective view illustrating a structure of the intra-body-cavity insertion instrument fastener according to the second embodiment of the invention.

FIG. 3A is a perspective view illustrating a structure of an intra-body-cavity insertion instrument fastener 38 according to the second embodiment of the invention.

The intra-body-cavity insertion instrument fastener 38 according to the present embodiment includes a pliable belt 40 in place of a snare loop 24 in an intra-body-cavity insertion instrument fastener 10 according to the first embodiment described above.

In case of the pliable belt 40, an intra-body-cavity insertion instrument inserted through inside of the pliable belt 40, e.g., a pliable insertion section 30 of a pair of pliable forceps 26 can be tightened by pulling a slider 34. Accordingly, a predetermined point of the pliable insertion section 30 can be thereby fixed to the intra-body-cavity insertion instrument fastener 38, as illustrated in FIG. 2.

As has been described above, the intra-body-cavity insertion instrument fastener 38 according to the second embodiment is also capable of preventing the pliable intra-body-cavity insertion instrument, e.g., the pair of pliable forceps 26 from moving.

Third Embodiment

Figure 3B:
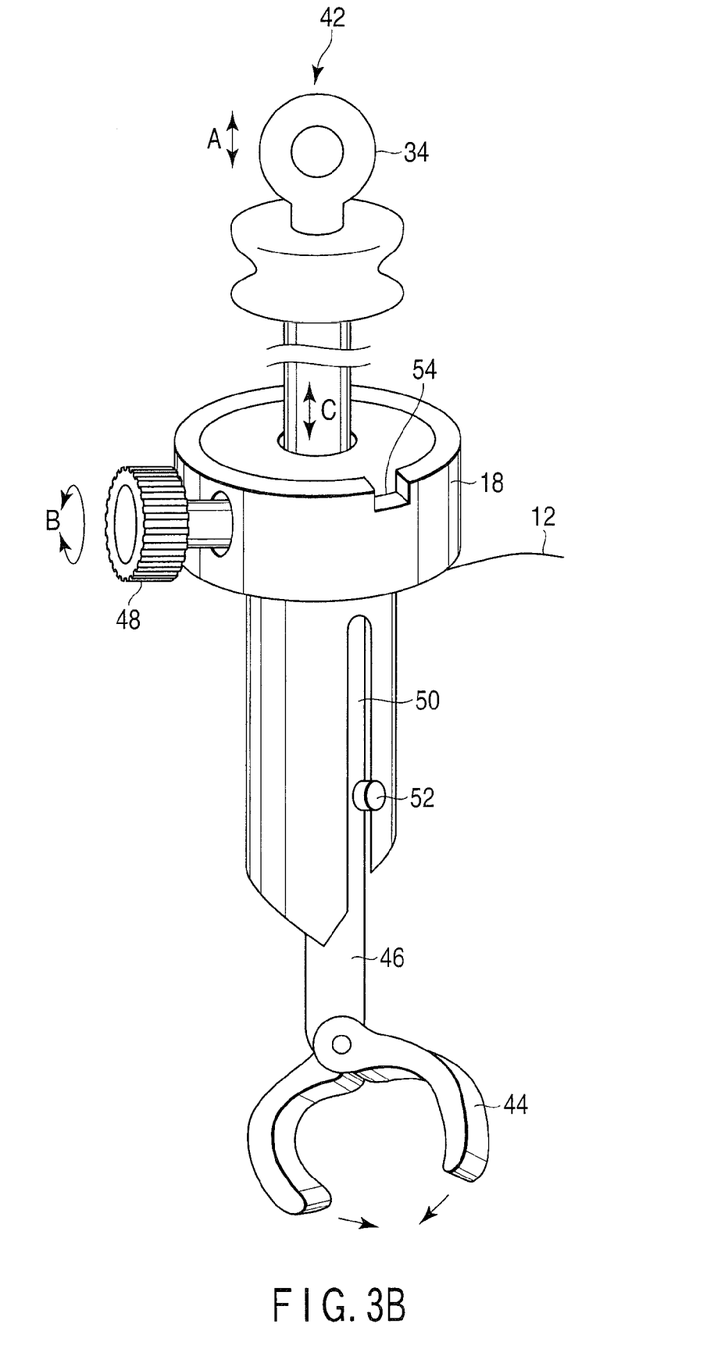
FIG. 3B is a perspective view illustrating a structure of the intra-body-cavity insertion instrument fastener according to the third embodiment of the invention.

FIG. 3B is a perspective view illustrating a structure of an intra-body-cavity fastener 42 according to the third embodiment of the invention.

The intra-body-cavity insertion instrument fastener 42 according to the present embodiment includes a fastener 46 having a mechanical pinch section 44 at a rear end of the fastener 46, in place of a sheath 20 and a snare loop 24 in a intra-body-cavity insertion instrument fastener 10 according to the first embodiment described previously. The pinch section 44 is configured to open/close by pulling/pushing a slider 34 provided at a rear end of the fastener 46, as denoted by an arrow A in the figure. To simplify the figure, the fastener 46 is illustrated as a simple shaft. Needless to say, however, the fastener 46 includes a known open/close mechanism in actual.

The fastener 46 is configured to lock/release retraction, as denoted by an arrow C in the figure, by rotating, as denoted by an arrow B in the figure, a dial 48 provided at a part of the insertion section 18, which is exposed to outside of the human body. That is, the position of the pinch section 44 is adjustable depending on a depth from the body wall 12 to an intra-body-cavity insertion instrument to be fixed, gripped by the pinch section 44, e.g., to the pliable insertion section 30 of the pliable forceps 26. A slit 50 is provided at a part of the insertion section 18 which is positioned in a body cavity 16 of the insertion section 18. A protrusion 52 engaged in the slit 50 is provided on the fastener 46. A motion path of motion of the protrusion 52 accompanied by retraction of the fastener 46 is regulated by the slit 50, so that direction of the pinch section 44 is always constant in relation to the slit 50. Further, an index 54 is provided at a position of a part of the insertion section 18 which is exposed to outside of the human body, wherein the position corresponds to the slit 50. In this manner, direction of the pinch section 44 can be grasped from outside of the human body.

As has been described above, the intra-body-cavity insertion instrument fastener 42 according to the third embodiment is also capable of preventing the pliable intra-body-cavity insertion instrument from moving, e.g., the pair of pliable forceps 26 from moving.

Fourth Embodiment

Figure 4A:
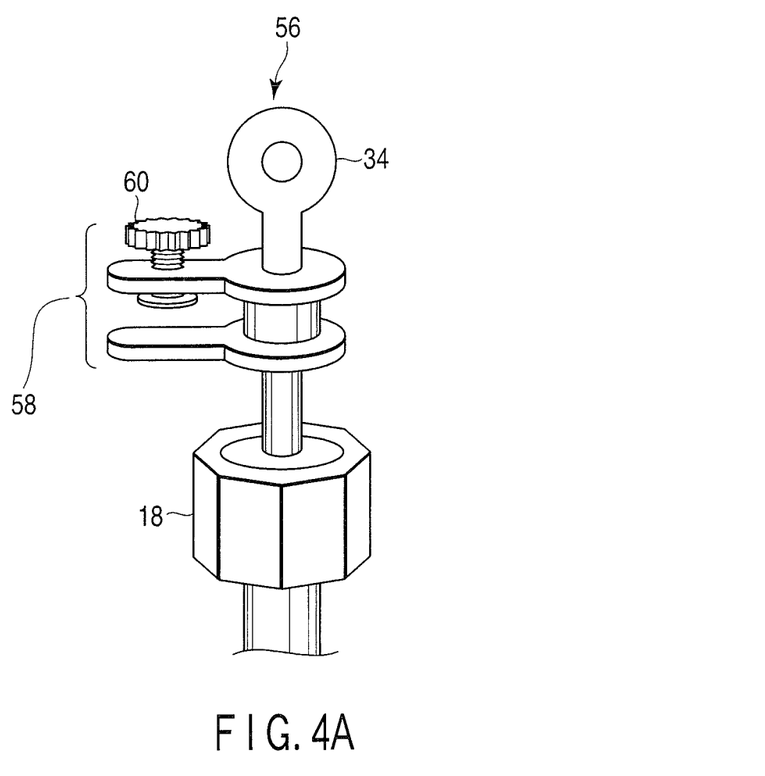
FIG. 4A is a perspective view illustrating a structure of an intra-body-cavity insertion instrument fastener according to the fourth embodiment of the invention.

FIG. 4A is a perspective view illustrating a structure of an intra-body-cavity insertion instrument fastener 56 according to the fourth embodiment of the invention.

In the intra-body-cavity insertion instrument fastener 56 according to the present embodiment, an external attachment section 58 is formed at a part of an insertion section 18 which is exposed to outside of the insertion section 18, in an intra-body-cavity insertion instrument fastener 10, 38, or 42 as described in the first to third embodiments described above.

The external attachment section 58 is used when the part of the insertion section 18 that is exposed to outside of the insertion section 18 is fixed a predetermined portion outside a human body. The external attachment section 58 is configured to be capable of clumping a to-be-clumped part outside a human body by tightening a screw 60.

Figure 4B:
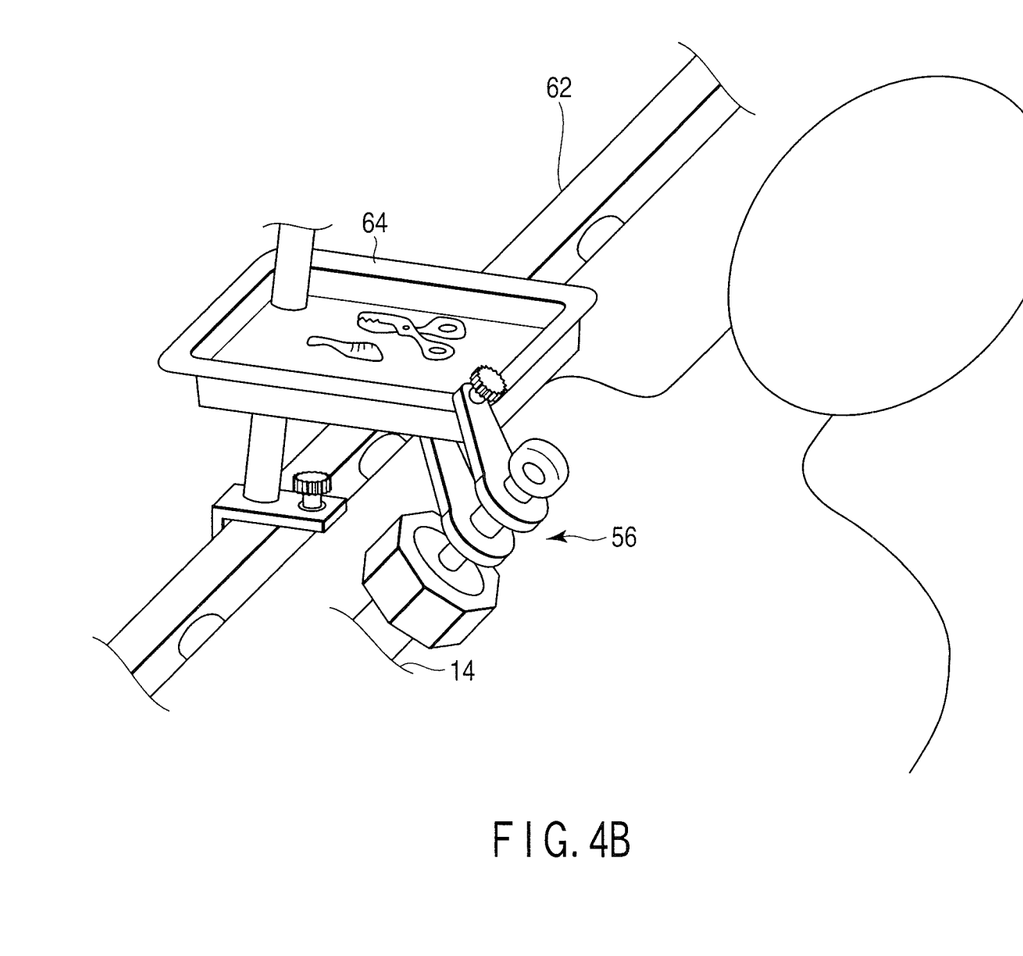
FIG. 4B is a view illustrating a use example of the intra-body-cavity insertion instrument fastener according to the fourth embodiment.

FIG. 4B is a view illustrating a use example of the intra-body-cavity insertion instrument fastener 56 according to the present embodiment. After inserting the insertion section 18 into a body cavity 16 from an insertion hole 14, the intra-body-cavity insertion section fastener 56 is fixed that the external attachment section 58 clumps a forceps tray 64 attached to a bed rail 62 provided on a side of a bed. After fixing the intra-body-cavity insertion instrument fastener 56 in this manner, a pliable intra-body-cavity insertion instrument, e.g., a pair of pliable forceps 26 is fixed, as has been described in the foregoing first to third embodiments.

As has been described above, the intra-body-cavity insertion instrument fastener 56 according to the fourth embodiment is capable of fixing more firmly a pliable intra-body-cavity insertion instrument, e.g., the pair of pliable forceps 26 by fixing, to a predetermined portion outside a human body, a part exposed to outside the human body.

The present invention has been described above on the basis of embodiments. However, the invention is not limited to the embodiments described above but may of course be variously modified or applied practically within the scope of the invention.

Additional Notes

Inventions as configured below can be extracted from the specific embodiments described above.

(1) An intra-body-cavity insertion instrument fastener comprising: an insertion section that is inserted into a body cavity and is held, partially exposed to outside of a human body; and a fastening section that fixes, to a predetermined position, a position of a predetermined point of an intra-body-cavity insertion instrument inserted into the body cavity from an insertion hole different from an insertion hole from which the insertion section is inserted into the body cavity, that the fastening section is formed at a top end of the insertion section.

Corresponding Embodiments

The first to fourth embodiments correspond to embodiments relate to the intra-body-cavity insertion instrument fastener described in (1). The body cavity 16 in these embodiments corresponds to the body cavity described above; the insertion section 18 corresponds to the insertion section described above; the insertion hole 14 corresponds to the latter insertion hole described above into which the insertion section is inserted; the insertion hole 14A corresponds to the different insertion hole described above; the pair of pliable forceps 26 corresponds to the intra-body-cavity insertion instrument described above; the groove section 22, snare loop 24, pliable belt 40, and fastener 46 correspond to the fastener described above; as well as the intra-body-cavity insertion instrument fasteners 10, 38, 42, and 56 correspond to the intra-body-cavity insertion instrument fastener.

Operation and Effects

According to the intra-body-cavity insertion instrument fastener described in (1), the intra-body-cavity insertion instrument which is flexibly deformed and easily inserted into the body cavity can be fixed when using the intra-body-cavity insertion instrument.

(2) The intra-body-cavity insertion instrument fastener described in claim 1, wherein the fastening section is capable of arbitrarily setting the position of the predetermined point of the intra-body-cavity insertion instrument.

Corresponding Embodiments

The first to fourth embodiments correspond to embodiments relate to the intra-body-cavity insertion instrument fastener described in (2).

Operation and Effects

According to the intra-body-cavity insertion instrument fastener described in (2), a fixing position can be arranged at an arbitrary position even if no adequate organ to which the insertion instrument is to be fixed in the body cavity. Therefore, a procedure can be performed stably.

(3) The intra-body-cavity insertion instrument fastener described in (1), wherein the fastening section includes a direction fixing instrument that fixes a direction of the intra-body-cavity insertion instrument in the body cavity.

Corresponding Embodiments

The first and third embodiments correspond to embodiments relate to the intra-body-cavity insertion instrument fastener described in (3). The groove section 22 or the slit 50 and the protrusion 52 in these embodiments correspond to the fastening section described above.

Operation and Effects

According to the intra-body-cavity insertion instrument fastener described in (3), not only the position of the intra-body-cavity insertion instrument is simply fixed but also the direction of the intra-body-cavity insertion instrument is fixed. Therefore, a procedure can be performed more stably.

(4) The intra-body-cavity insertion instrument fastener described in (1), wherein the insertion section is fixed to a body wall.

Corresponding Embodiments

The first to third embodiments correspond to embodiments relate to the intra-body-cavity insertion instrument fastener described in (4). The body wall 12 in these embodiments corresponds to the body wall described above.

Operation and Effects

According to the intra-body-cavity insertion instrument fastener described in (4), the position of the intra-body-cavity insertion instrument can be fixed relative to the body wall, and can accordingly be fixed relative to a target portion.

(5) The intra-body-cavity insertion instrument fastener described in (1), wherein the insertion section includes an attachment section for fixing, to a predetermined portion outside the human body, a part of the insertion section that is exposed to outside of the insertion section.

Corresponding Embodiments

The fourth embodiment corresponds to an embodiment relate to the intra-body-cavity insertion instrument fastener described in (5). The forceps tray 64 attached to the bed rail 62 in the embodiment corresponds to the predetermined portion outside the human body described above; as well as the external attachment section 58 corresponds to the attachment section described above.

Operation and Effects

According to the intra-body-cavity insertion instrument fastener described in (5), movement of the intra-body-cavity insertion instrument can be fixed more rigidly.

What is claimed is:

1. An intra-body-cavity insertion instrument fastener for fixing an intra-body-cavity insertion instrument inserted into a body cavity from a first insertion hole, the intra-body-cavity insertion instrument fastener comprising:
    an insertion section configured to be inserted into the body cavity from a second insertion hole different from the first insertion hole, and to be held partially exposed to an outside of the body cavity;
    a sheath configured to be protruded from a top end of the insertion section;
    a groove surface formed at a top end of the sheath, wherein the groove surface defines a groove shaped to complement a portion of the intra-body-cavity insertion instrument; and
    a grasp section extending from the groove surface, wherein the grasp section is configured to grasp the portion of the intra-body-cavity insertion instrument to fix the position of the portion with respect to the groove surface and to move the portion into complementary engagement with the groove surface to fix the orientation of the portion with respect to the groove surface.

2. The intra-body-cavity insertion instrument fastener according to claim 1, wherein the grasp section includes a snare loop through which the portion of the intra-body-cavity insertion instrument can be arranged, wherein the snare loop is connected through the sheath to a slider and the snare loop is configured to tighten by operation of the slider to grasp the portion and to move the grasped portion into complementary engagement with the groove surface.

3. The intra-body-cavity insertion instrument fastener according to claim 1, wherein the groove defined by the groove surface has a predetermined orientation and the portion of the intra-body-cavity insertion instrument is fixed to the predetermined orientation when the portion is moved into complementary engagement with the groove surface.

* * * * *